United States Patent
Kim et al.

(10) Patent No.: US 10,640,744 B2
(45) Date of Patent: May 5, 2020

(54) ELECTROMECHANICAL LYSIS OF BACTERIAL PATHOGENS USING ION CONCENTRATION POLARIZATION

(71) Applicant: Massachusetts Institute of Technology, Cambridge, MA (US)

(72) Inventors: Minseok Kim, Medford, MA (US); Jongyoon Han, Bedford, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 159 days.

(21) Appl. No.: 15/728,860

(22) Filed: Oct. 10, 2017

(65) Prior Publication Data

US 2018/0371400 A1    Dec. 27, 2018

Related U.S. Application Data

(60) Provisional application No. 62/523,404, filed on Jun. 22, 2017.

(51) Int. Cl.
*C12N 13/00* (2006.01)
*C12N 1/06* (2006.01)

(52) U.S. Cl.
CPC .............. *C12N 1/06* (2013.01); *C12N 13/00* (2013.01)

(58) Field of Classification Search
None
See application file for complete search history.

(56) References Cited

U.S. PATENT DOCUMENTS

| 9,850,146 | B2 | 12/2017 | Choi et al. |
| 2014/0374274 | A1 | 12/2014 | Kwak et al. |
| 2016/0115045 | A1 | 4/2016 | Kim et al. |
| 2018/0141832 | A1 | 5/2018 | Choi et al. |

OTHER PUBLICATIONS

Jannasch ("Bacterial Populations in Sea Water as Determined by Different Methods of Enumeration" Limnology and Oceanography, 1959, 128-139). (Year: 1959).*
Kim, S.J., et al., "Nanofluidic Concentration Devices for Biomolecules Utilizing Ion Concentration Polarization: Theory, Fabrication, and Applications," Chem Soc Rev, 39(3): pp. 912-922 (2010).
Kim, S.J., et al., "Direct Seawater Desalination by Ion Concentration Polarization," Nature Nanotechnology, vol. 5, pp. 297-301 (2010).

* cited by examiner

*Primary Examiner* — Robert J Yamasaki
*Assistant Examiner* — Charles Zoltan Constantine
(74) *Attorney, Agent, or Firm* — Elmore Patent Law Group, P.C.; Carolyn Elmore; Mahreen Hoda

(57) ABSTRACT

Scalable, high throughput and power-efficient electromechanical lysis using low electric potential, which can be used for harvesting valuable intracellular biomolecules (DNA, RNA, and proteins) and metabolites (e.g., biodiesels, bioplastics, antibiotics, and antibodies), and for sterilizing large volume solutions (e.g. disinfection of bacterial contaminated drinking water). The method can be directly integrated with other microfluidic devices for all-in-one, fully integrated total-analysis systems for various bacterial (and cellular) studies and clinical applications.

15 Claims, 15 Drawing Sheets
(14 of 15 Drawing Sheet(s) Filed in Color)

ELECTROMECHANICAL LYSIS OF BACTERIAL PATHOGENS USING ION CONCENTRATION POLARIZATION

RELATED APPLICATION

This application claims the benefit of U.S. Provisional Application No. 62/523,404, filed on Jun. 22, 2017. The entire teachings of the above application are incorporated herein by reference.

GOVERNMENT SUPPORT

This invention was made with Government support under Grant No. R01 AI117043 awarded by the National Institutes of Health. The Government has certain rights in the invention.

BACKGROUND OF THE INVENTION

Lysis is the disruption of the cell membrane, which is a standard process for not only eliminating pathogens but also accessing intracellular contents such as nucleic acids, proteins, metabolites, and other organelles. In particular, the extracted biomolecules from mammalian or microbial cells provide essential information about genetic or disease characteristics[1]. Thus, the cell lysis is the first procedure for various biological and clinical studies, including genomics, proteomics and metabolomics, with a wide range of applications in medicine and pharmacy, water-food-energy industry, agriculture, and for recovering valuable intracellular products from recombinant cells.

Many conventional techniques have been developed to secure the highest yield and purity of the lysates from various organisms; among them, chemical, mechanical, and other physical methods were commonly employed. Chemical (detergents) or enzymatic permeation of the cell membrane was an attractive way of recovering lysates due to the simple operation and high lysis efficiency[2-4], but the added reagents and proteins often hindered particular reactions and/or damaged lysates, resulting in narrow choices for downstream assays[5]. In addition, the chemical composition and concentration needed to be specifically optimized according to organisms so that it was difficult to be applicable for globally lysing various species in a complex cell mixture. By contrast, mechanical methods such as bead beating[6,7] and sonication[8,9], versatilely lysed any cell types without addictive ingredients[10]; however, they often require bulky and expensive equipment, and the lysis efficiency and recovery rate of lysates fluctuated greatly due to uncontrollable mechanical shearing of released intracellular biomolecules according to the apparatus and operational conditions[8,11]. Moreover, it was often inefficient to apply the conventional mechanical lysis, which required somewhat large volume solutions to operate (>1 mL), using modern biochemical analysis tools (e.g., Nanostring) that only utilized a small quantity of samples (<50 μL) for executing genetic analysis[12].

Electrical cell lysis would be a preferred method for microfluidic systems because the operational setting was simple without lytic additives and enabled prompt lysis using a sub-microliter solution with a wide range of cellular density (1-10$^7$ cells/mL)[5,13]. Furthermore, the miniaturized electrical lysis module was directly integrated with post-processing elements, resulting in on-line, all-in-one, in-situ, and accurate analysis of the lysates[14]. However, for small cells such as bacteria (approximately 1 μm long and 0.5 μm thick), the required electric field was extremely high (>15 kV/cm)[15] in order to satisfy the transmembrane potential for lysis (~1.5 V)[16], which might induce negative effects associated with high electric power, including biomolecule degradation, Joule heating, and water dissociation.

To alleviate the issues, the bacterial lysis by an electric field was only performed either in a low salinity solution (e.g., distilled water)[17] for minimizing the current density or using a pinched microchannel (25 μm width)[18] and small electrode gap (10-20 μm)[19,20] to reduce the electric potential. This eventually required additional steps to exchange buffers, and resulted in extremely low lysis throughput (<1 μL/min)[18,20-22]. In this context, it was difficult for electrical lysis to produce enough quantity of lysates to implement off-chip post processing and analysis such as mass spectrometry or capillary electrophoresis, which generally required at least 100 μL solutions for handling. Recently, electrical cell permeation that also takes advantage of mechanical agitation (vortex) was reported to minimize the required electric field for permeating the membrane of mammalian cells[23]. However, challenges still exist in achieving reliable bacterial lysis that can be versatile and yet generally applicable to a wide range of bacterial pathogens, utilizing a low electric field and providing high throughput.

SUMMARY OF THE INVENTION

Here we disclose a novel bacterial lysis mechanism to take advantages of both mechanical shearing and electrical permeation, so called "electromechanical lysis", enabling a rapid, continuous, versatile, and high-throughput lysis of hard-to-lysis bacterial pathogens by only applying substantially low electrical potentials (a few tens volts). Our invention involves the following specific innovations and technological advances:

1. Demonstration that Ion Concentration Polarization (ICP) generated near Ion Selective Membranes (ISMs)[24,25] facilitates electrical lysis of bacterial cells, owing to formation of anomalously fast electroconvective vortexes[25-27]. The electroconvective vortex concentrated and agitated bacterial cells toward the ISM walls where electric fields and ionic concentrations were spatiotemporally enhanced and fluctuated[26-28], inducing additional mechanical shearing and bombardment by the ISMs.
2. Characterization of the bacterial lysis in various electrical and ionic conditions, and demonstration that a low electric field (20-60 V) enables bacterial lysis, resulting in not only minimization field-associated negative effects but also utilization of highly salted solutions (e.g., 150 mM buffer).
3. Operation of the electromechanical lysis in a continuous and programmed manner to achieve the higher lysis throughput and lysate yield.
4. Successful recovery of intracellular biomaterials such as proteins and Ribonucleic acids (RNAs) from both easy-to-lysis (*Escherichia coli, E. coli*) and hard-to-lysis (*Mycobacterium smegmatis, M smeg*) bacterial pathogens that typically required extremely high electric potentials (e.g., 10-20 KV/cm)[15,17].
5. Demonstration that a microfluidic lysis device can be highly scaled-up due to the simple operational principle that only required a fluidic channel between two ISMs, resulting in ultra-high-throughput (>1 mL/min) electrical lysis of bacterial pathogens in a power-efficient and portable manner.

The invention encompasses a method of lysing a cell membrane comprising the steps:

a. directing a fluid stream containing cells in a channel comprising an inlet and an outlet and defined, at least in part, by at least a first ion exchange membrane and at least a second ion exchange membrane, wherein the ion exchange membranes are juxtaposed and characterized by the same charge;

b. applying an electric field across the channel at a voltage and duration sufficient to cause helical electroconvective vortex formation across the channel, thereby lysing the cell membranes of the cells;

c. collecting a fluid stream comprising lysate; and d. isolating or collecting the lysate.

Since lysis is the starting point of various post analysis of bacterial cells, the invention would have a wide impact on not only fundamental studies on biomolecular studies but also industrial applications including, but not limited to, water disinfection, wastewater treatment, aquarium cleaning, food/beverage sterilization and recovery of valuable metabolites in biorefinery and pharmaceutical industries.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1A:
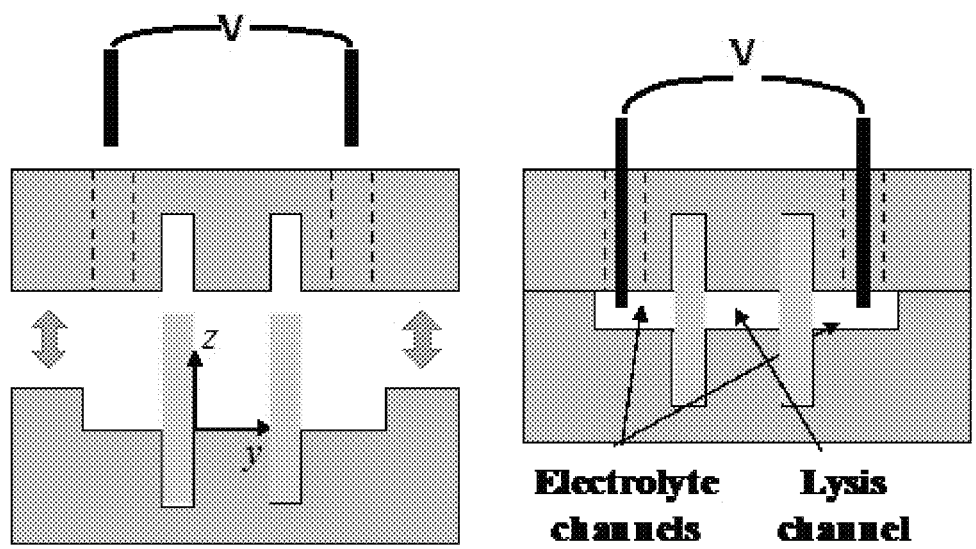
FIG. 1A-1D, collectively referred to herein as FIG. 1, views A, B, C and D: A) Fabrication of membrane-integrated microfluidic lysis devices; B) Schematic illustration describing principle of electromechanical lysis for bacterial cells using electroconvective vortices; C) Microscopic observation of electromechanical lysis at Bacterial Lysis Zone (BLZ); D) Close-up observation of aggregated bacterial chunks that were subject to convectional shear flow, mechanical bombardment to the membrane and concentrated electric power, leading to bacterial lysis within a second.

A description of preferred embodiments of the invention follows.

The invention encompasses a method of lysing a cell membrane and methods of removing bacteria from a fluid stream, including, for example, a method of disinfecting water and a method of treating wastewater. The methods comprise the use of Ion Concentration Polarization (ICP) generated near Ion Selective Membranes (ISMs) to induce electrical lysis of bacterial cells. Ion Concentration Polarization has been described, for example, in Kim et al., Nat Nanotechnol 5, 297 (2010) and U.S. Pat. App. Pub. No. 20140374274 A1 (entitled "WATER DESALINATION/PURIFICATION AND BIO-AGENT PRECONCENTRATION BY ION CONCENTRATION POLARIZATION"), the contents of each of which are expressly incorporated by reference herein. Ion exchange membranes (IEMs) act as an ion filter by allowing only cations or anions to pass through. This selective ion transport initiates a unique phenomenon called ion concentration polarization (ICP) near the membranes, which is characterized by significant, dynamic perturbation in ion concentrations (also known as ion depletion and ion enrichment).

The ion exchange membranes are cationic or anionic exchange membranes. The two membranes can be the same or different. Strong anion or cation exchange membranes, as those products are generally sold in the art, are preferred. NAFION™ membranes, FUMASEP® FTAM-E and FTCM-E (FuMATech CmbH, Germany) are suitable membranes. However, others can also be used. In particular, the term "ion exchange membrane" is intended to include not only porous, microporous or nanoporous films, but also resins or materials through which ions can pass. Thus, in one embodiment, an ion exchange resin can be entrapped by one or more meshes (or porous membranes) in lieu of or in addition to one or more of the ion exchange membranes.

The ion exchange membranes can be placed into a support, such as glass, polydimethylsiloxane (PDMS), or other inert material. Thus, the support can also contribute to the formation of the channels.

The first channel (defined by the ISMs) can, for example, be a microchannel.

The electric field can be created by an electrode and a ground each located external and parallel to the channel. In general, the electrode forms a second channel with the first of said two juxtaposed ion exchange membranes and the ground forms a third channel with the second of said two juxtaposed ion exchange membranes. These channels are generally filled with an electrolyte solution, for example, phosphate buffered saline (PBS).

The lysis can be conducted in a batch, continuous, or semi-continuous manner. In certain aspects, the lysis is conducted in continuous manner. In certain additional aspects, the lysis is a semi-continuous electromechanical lysis process. For example, the fluid stream comprising the cells can be directed to the first channel at a semi-continuous flow.

The methods can be used to isolate intracellular biomolecules, including, but not limited to, DNA, RNA, and proteins, and/or to isolate or harvest bacterial metabolites including, for example, biodiesels, bioplastics, antibiotics, and antibodies. The method can further comprise isolating a bacterial protein and/or a bacterial nucleic acid (for example, RNA) from the lysate.

The invention also encompasses a method comprising the use of a plurality or channels in parallel, each defined by an ion exchange membrane.

Working Principle of Electromechanical Lysis

FIG. 1A illustrates the fabrication procedure of the ISMs-integrated microfluidic devices. First, two cation exchange membranes (CEMs) that define a bacterial loading channel for lysis (lysis channel) are integrated with two electrolyte rinsing channels to apply electric fields (electrolyte channels), according to our previous ISM-integration technique[25, 29]. Thus, the CEMs act as side walls of the lysis channels while the top and bottom surfaces were made of Polydimethylsiloxane (PDMS). The top and bottom PDMS blocks were prepared with microchannels (height, h=250 μm) and/or high-aspect-ratio membrane slots (thickness, $t_{slot}$=0.45 mm, $h_{slot}$=3.5 mm) where two CEMs ($t_{Mem}$=0.45 mm, $h_{Mem}$=7 mm) were inserted, followed by an irreversible bonding process. No fluid leakage through the gap between CEMs and membrane slots was observed because the CEMs were swelled and tightly filled the gap after hydration[25].

Figure 1B:
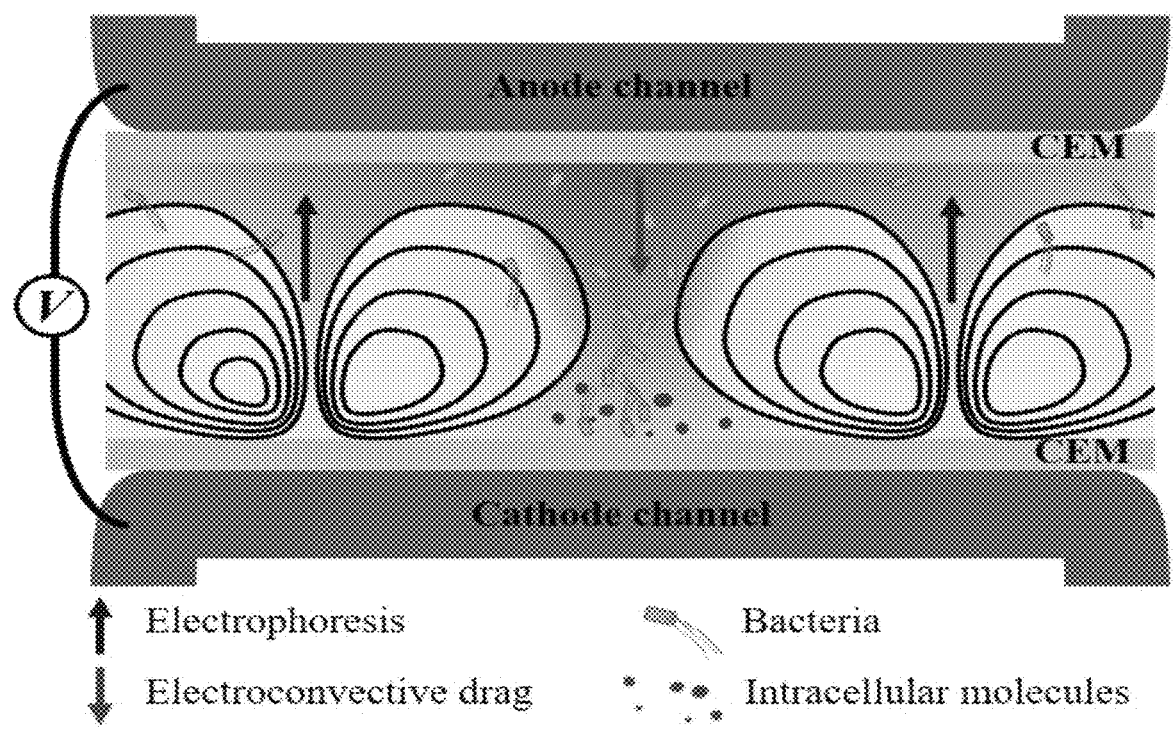
Figure 1C:
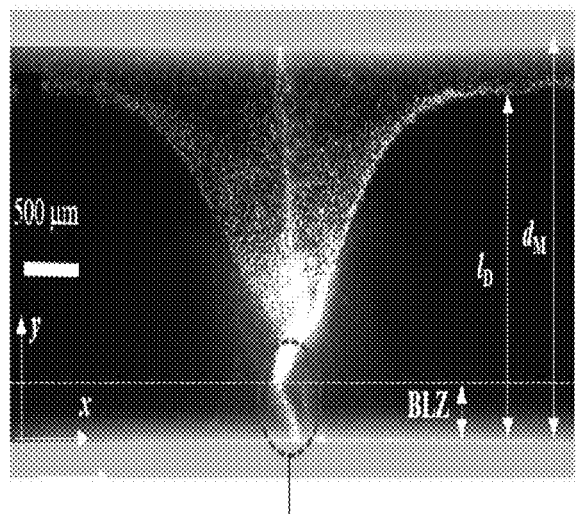

FIG. 1B shows an experimental setup and working principle of the electromechanical lysis of bacterial cells. Once an external electric field was applied by inserting an electrode probe set at reservoirs of the electrolyte channels, the anodic and cathodic CEMs achieved approximately equivalent potentials to the anode and cathode, respectively. This is because a highly conductive electrolyte (phosphate buffered saline, PBS 1.5 M) was introduced to the electrolyte channels, helping to maintain nearly constant chemical environments, minimizing the ICP effects at the electrolyte channels, and efficiently forming ICP only at the lysis channel. Given the electrical and ionic setting, both ion depletion and ion enrichment regions were generated at the lysis channel near cathodic and anodic CEMs, respectively[29]. Bacterial cells in the lysis channel initially drawn to the anodic CEM due to electrophoresis, then concentrated into a small spot between two fully-expanded ion depletion (vortex) regions, forming an inverted-triangular-shaped bacterial plug (FIG. 1C). After the concentrated bacterial plug was fully developed, the maximum ion depletion length ($l_D$) was almost close to the membrane-to-membrane distance ($d_M$=2 mm). However, the ion depletion length was almost zero at the sharp tip (red-dashed circle of FIG. 1C) of the concentrated bacterial plug because the electroconvective vortices continuously delivered bacterial cells toward the immediate vicinity (termed Bacterial Lysis Zone or BLZ) of the cathodic CEM. Interestingly, the bacterial motion at the BLZ was extremely fast and chaotic due to electrokinetic instabilities at the region.

Figure 1D:
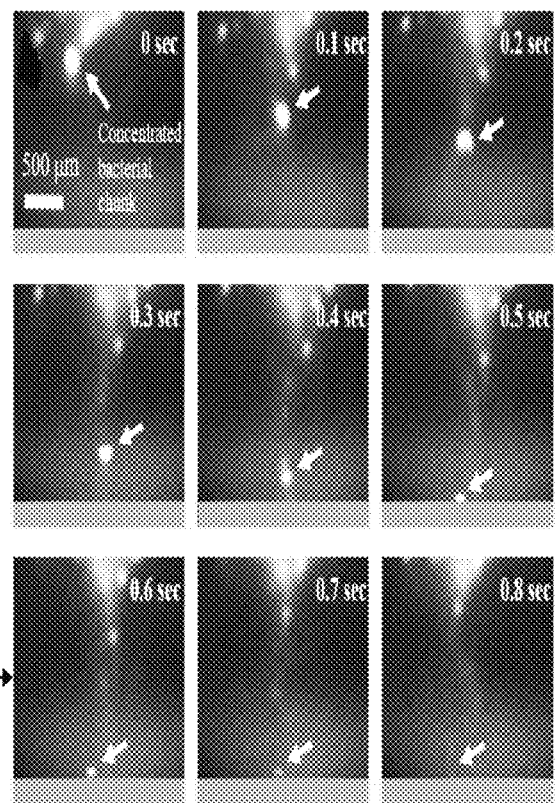

Consequently, the bacterial cells were exposed to spatiotemporally unstable electrical and fluidic fields, resulting in bacterial lysis by the electrical and mechanical synergic forces. FIG. 1D shows microscopic observation of the bacterial lysis at the BLZ; first, bacterial cells were concentrated and formed bacterial chunks at the sharp tip of the bacterial plug, and then gradually lysed within a second.

Visualization and Quantification of the Lysis Performance

Figures 2A, 2B:
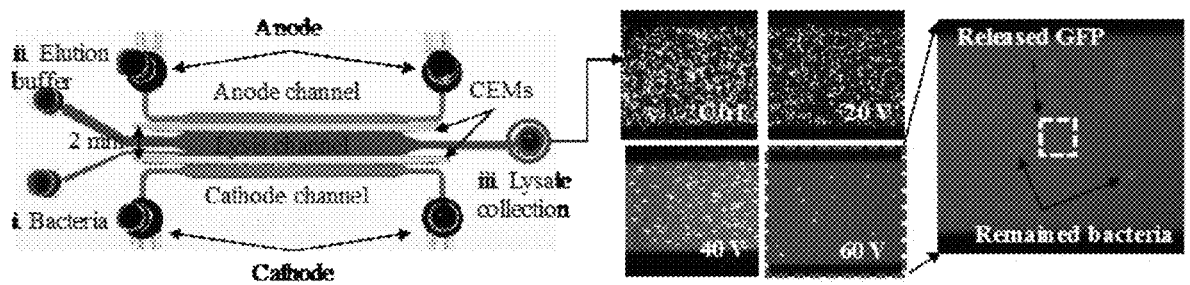
FIG. 2A-2F, collectively referred to herein as FIG. 2, views A, B, C, D, E and F: A) Experimental setup for quantification of lysis efficiency (bacterial removal rate) and lysate yield (GFP recovery rate); B) Fluorescent microscopic images after the electromechanical lysis in various operational conditions; C) Time-lapse in-situ images of the lysis, starting from homogeneously distributed bacterial cells and leading to fully-lysed concentrated GFP plugs; D-F) Quantitative lysis results in various electric potentials and operational times, which exhibited three dominant ranges: Insufficient (D), Appropriate (E), and Excessive (F).

FIG. 2A provides a schematic of the experimental setup used for performance testing. Done in batch mode, the process generally followed three steps: i) bacterial loading and lysis; ii) elution of lysates and un-lysed remaining cells; and iii) collection and quantification by fluorescent signals and image processing. Lysis performance metrics, such as lysis efficiency (rate of bacterial removal) and lysate yield (rate of lysate recovery) were quantified using constitutively green fluorescent proteins (GFP)-expressing E. coli (~$10^8$-$10^9$ cfu/mL).

Figure 2C:
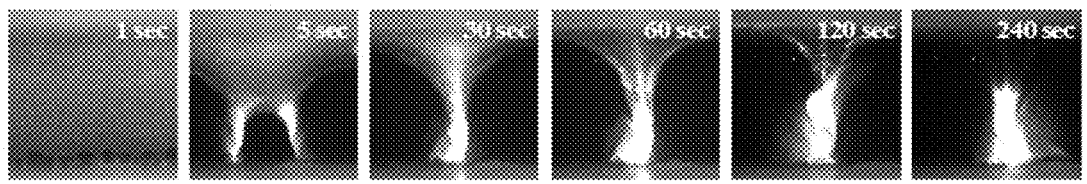
Figure 2D:
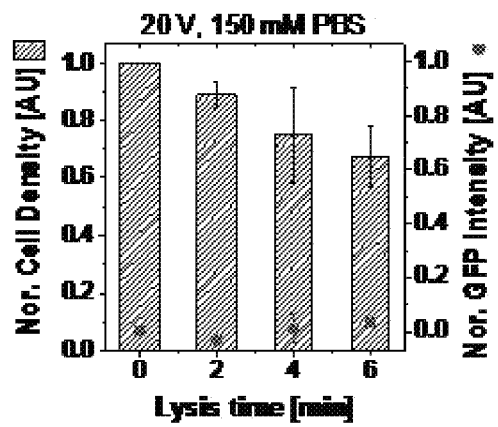
Figure 2E:
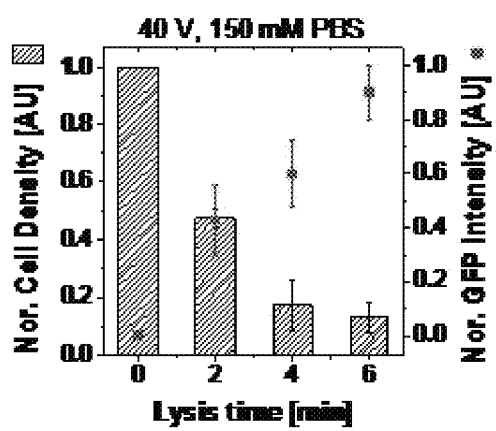
Figure 2F:
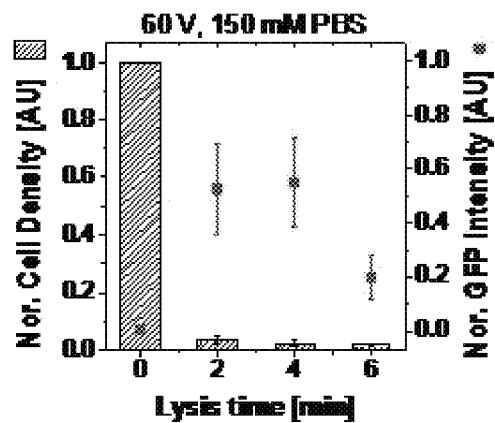
Figure 3A:
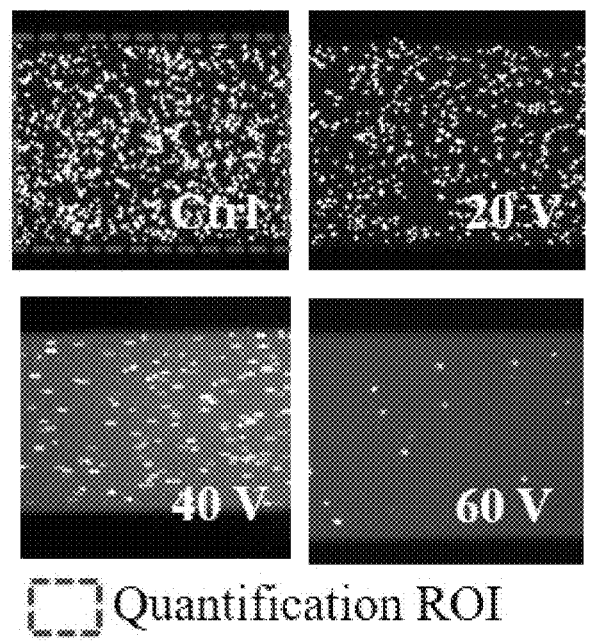
FIG. 3A-3D, collectively referred to herein as FIG. 3, views A, B, C and D: A) Fluorescent microscopic images after the electromechanical lysis using a highly salted solution (150 mM PBS buffer); B, C, D) Quantification of lysis performance using a highly salted solution (150 mM PBS buffer) and different electrical potentials: 20V (B), 40V (C) and 60V (D).
Figure 3B:
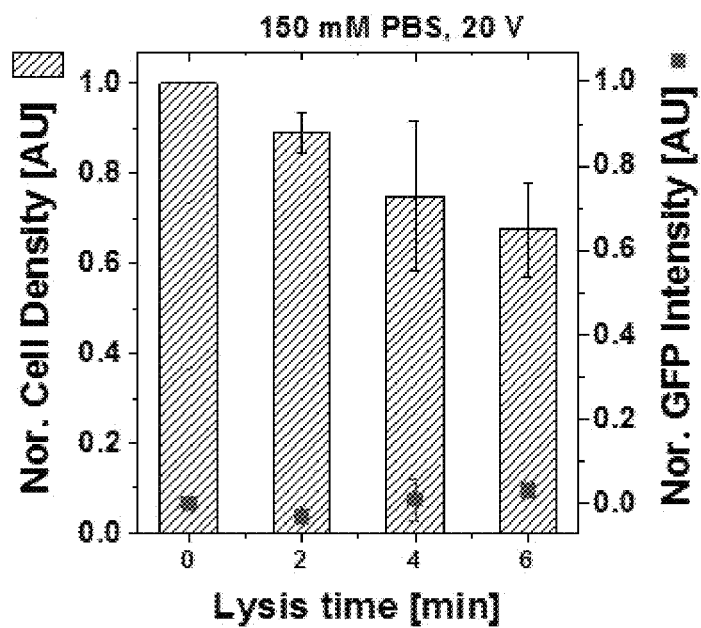
Figure 3C:
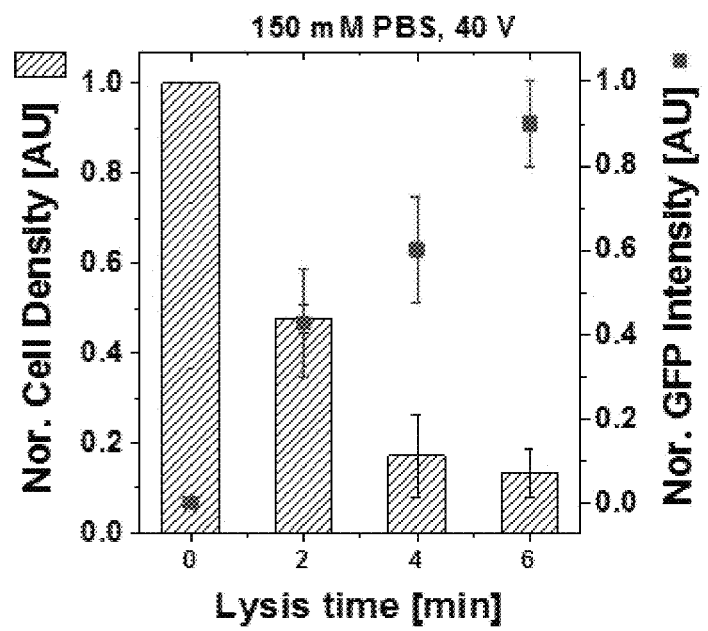
Figure 3D:
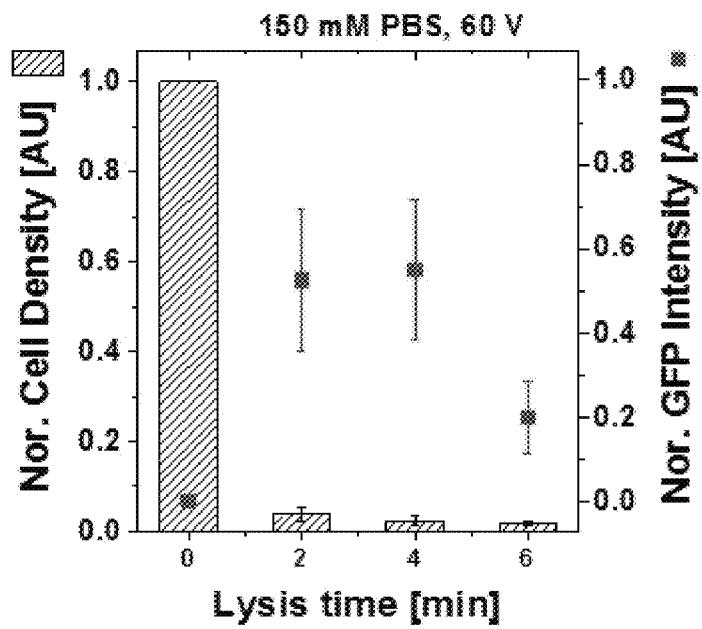

A bacterial solution (~5 μL) was introduced to the lysis channel and a DC electric potential (20-60 V) was applied across the electrolyte and lysis channels (i). After lysis, the lysis channel was flushed with an elution buffer (100 μL, 1×PBS) (ii). Lysates and remaining bacterial cells at the outlet reservoirs were then collected for quantification (~105 μL) (iii). Both bacterial population and background GFP intensity were measured before and after the lysis process by simple image processing. The un-lysed bacterial cells showed higher GFP intensity than the background (red spots in FIG. 2B), while the GFP intensity in the background fluid corresponded to the amount of intracellular GFP released by the lysis (green color in FIG. 2B). During the lysis process, the bacterial cells made concentrated bacterial plugs between the vortices and lysed at the BLZ in the cathodic CEM within 6 min (FIG. 2C). FIGS. 2D-2F show results of the electromechanical lysis that revealed effects of the electric fields intensity, operational time, and buffer concentration. The higher field strength enabled the faster formation of the concentrated bacterial plug and stronger electroconvective vortices, leading to more rapid bacterial lysis. The longer operation time showed the higher bacterial lysis efficiency (removal rates), which was quantified by measuring remaining cell numbers after the lysis. However, the long exposures to the relatively high electric potential (60 V) resulted in reduction of the GFP yields even though the lysis efficiency remained over 95%, presumably due to the GFP degradation at the over-processing conditions. Thus, there was a trade-off relationship between the lysis efficiency and lysate yields, which was optimal in the moderate potential (40 V) for 4-6 min operation time.

Distinguishingly, bacterial lysis was enabled within a few minutes by applying only 20-60 volts across the electrolyte and lysis channels, which is an extremely small electric field strength (100-300 V/cm) compared to that required for previous electrical lysis techniques for bacterial cells (10-20 kV/cm)[15]. It is noted that the electric field of the electromechanical lysis was estimated by assuming no potential loss at the electrode-electrolyte interfaces and along the electrolyte channel, so that the actual portion consumed for the bacterial lysis would be lower than the calculated value. In this context, our electromechanical approach enabled bacterial lysis by only applying a small electric field (<100 V/cm), which was at least 100 times lower electric field than previous bacterial lysis using an electric field. This may be attributed to the additional mechanical shearing applied to bacterial cells by the electroconvective vortices in addition to the applied electric effect that was efficiently focused on the tip of concentrated bacterial plug by the ICP phenomena. Furthermore, as shown in FIGS. 3A-3D, the lysis operated using even a highly salted solution such as 150 mM PBS buffer. This is normally difficult because the high current density typically causes water dissociation-related problems such as bubble generation, lysate degradation, and pH shift. The capability to lyse the bacterial cells in a highly salted buffer is valuable because the lysis step can be directly and immediately implemented after bacterial culture and/or preparation without buffer exchange steps to manage the salt concentration, implying the high possibility of on-line, in-situ, and fully-integrated electrical lysis.

Continuous and Programmed Electromechanical Lysis

Figure 4A:
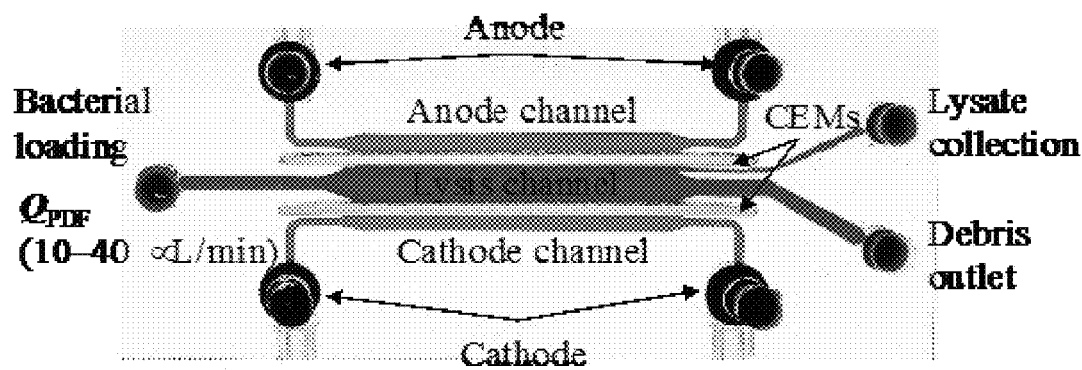
FIG. 4A-4E, collectively referred to herein as FIG. 4, views A, B, C, D and E: A) Experimental setup for continuous lysis operation; B) Fluorescent microscopic images along the lysis channel; C) Collected GFP and other lysates using continuous lysis; D, E) Quantification of continuous lysis performance using different electrical potentials: 40V (D) and 80V (E).
Figure 4B:
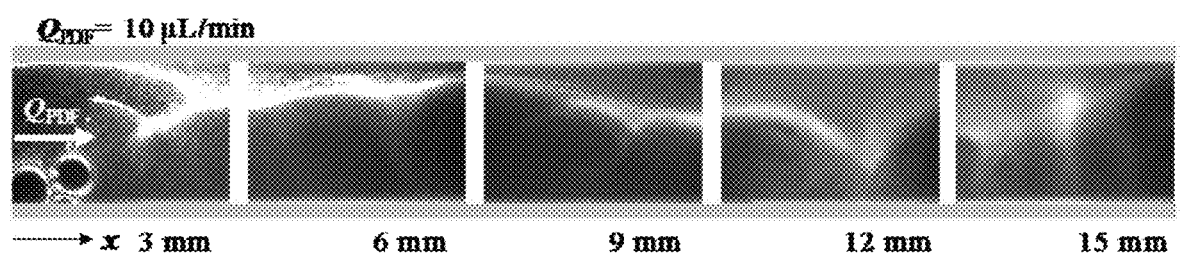
Figure 4C:
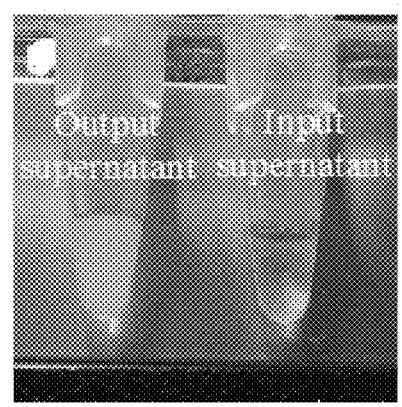
Figure 4D:
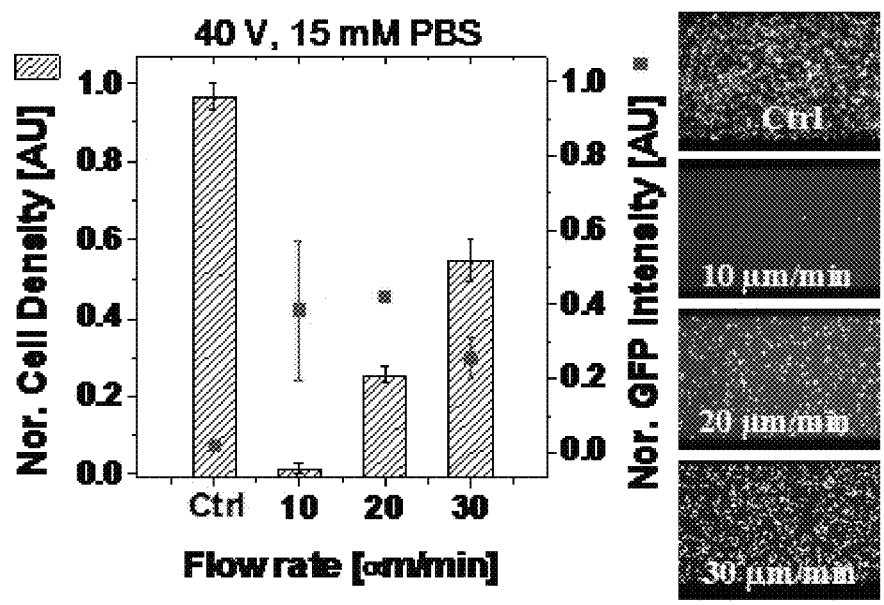
Figure 4E:
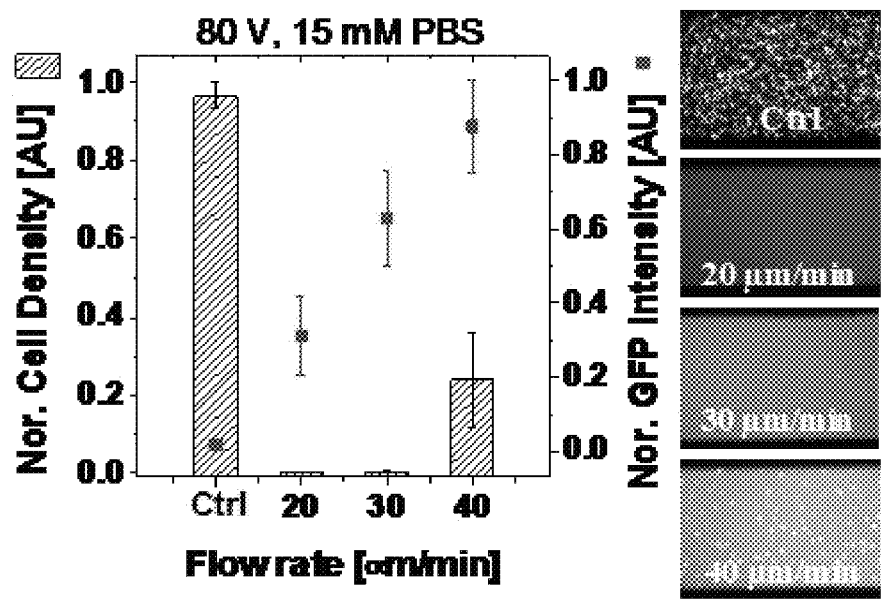

One limitation of the previously described batch-type lysis operation is the requirement of an elution step, leading to unavoidable lysate dilution and discretized operation. To address this, a continuous electromechanical lysis process was developed, which maintains a balance between applied electric fields and bacterial flow rates. FIG. 4A shows the experimental setup for continuous operation. A pressure driven flow ($Q_{PDF}$=10-40 μL/min) continuously delivered bacterial cells to the lysis channel where a DC electric field was applied to generate the complex and chaotic vortex patterns found in the over-limiting ICP phenomena[25]. Upon entering the lysis channel, the bacterial cells were transported toward the anodic CEM by electrophoresis, and then gradually lysed by being trapped to the electroconvective vortices along the 15-mm-long channel, resulting in continuous collection of lysates (GFP) at the downstream outlet (FIGS. 4B, 4C). The relatively high QPDF decreased the time of exposure to the vortices and electric field, reducing the GFP yield and lysis efficiency (FIG. 4C). The GFP yield was also reduced when the flow rate was slower than an optimal value (20 μL/min at 40 V) because of too long exposure to the vortices although it increased the bacterial lysis efficiency (FIG. 4D). At a higher field potential (80 V), a higher flow rate (40 μL/min) was used to achieve the maximum GFP yield (FIG. 4E). Over 75% GFP recovery was achieved, which was measured by comparing fluorescent intensity before and after the lysis channel.

Figure 5A:
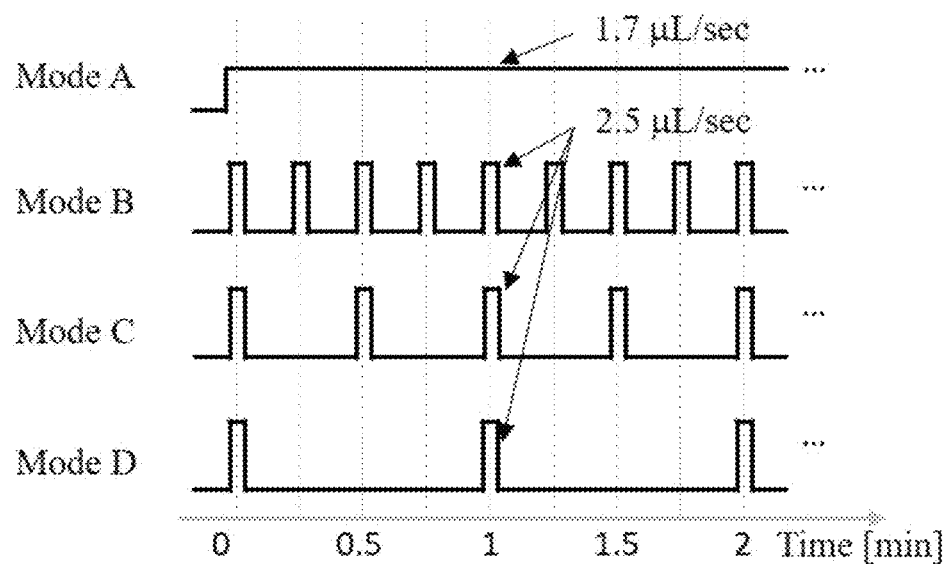
FIG. 5A-5C, collectively referred to herein as FIG. 5, views A, B and C: A) Control parameters of bacterial loading modes via programmed syringe pump; B) 5-pane view (L-R) of mode results, with pane 1 depicting the control, pane 2 depicting continuous (mode A), and panes 3-5 depicting semi-continuous modes B-D respectively; C) Quantitative results of the various modes.
Figure 5B:
Figure 5C:
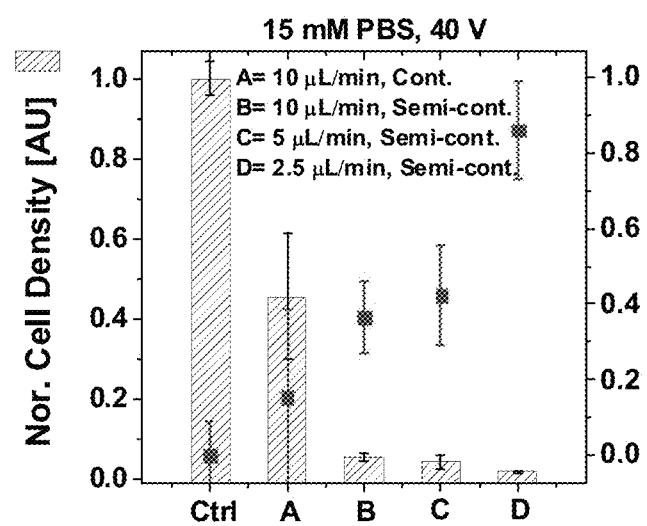

FIGS. 5A-5C depict operating parameters and results for a semi-continuous lysis mode that can take advances of both batch and continuous operation. That is, the semi-continuous is the continuous and automated repetition of the batch electromechanical lysis by programming $Q_{PDF}$, without the use of an elution buffer. The unit volume for sample loading was fixed at 2.5 μL while the loading frequency using a programmed syringe pump was varied among the modes, resulting in flow rates of 2.5-10 μL/min (FIG. 5A). Because some bacterial cells were not trapped by the electroconvective vortices but freely flowed along the channel by the $Q_{PDF}$ during the continuous lysis mode, it was difficult to simultaneously achieve both high lysate yield (GFP recovery rate) and high lysis efficiency (bacterial removal rate). By contrast, the semi-continuous method allowed a time for which the bacterial cells moved toward the BLZ by the electroconvective drag, leading to improved performances compared to the continuous method. As shown in FIGS. 5B and 5C, we achieved high GFP yield as well as high lysis efficiency from GFP-expressing E. coli (~5×10[8] cfu/mL) using the semi-continuous modes.

RNA Recovery from Various Bacterial Strains

Figure 6A:
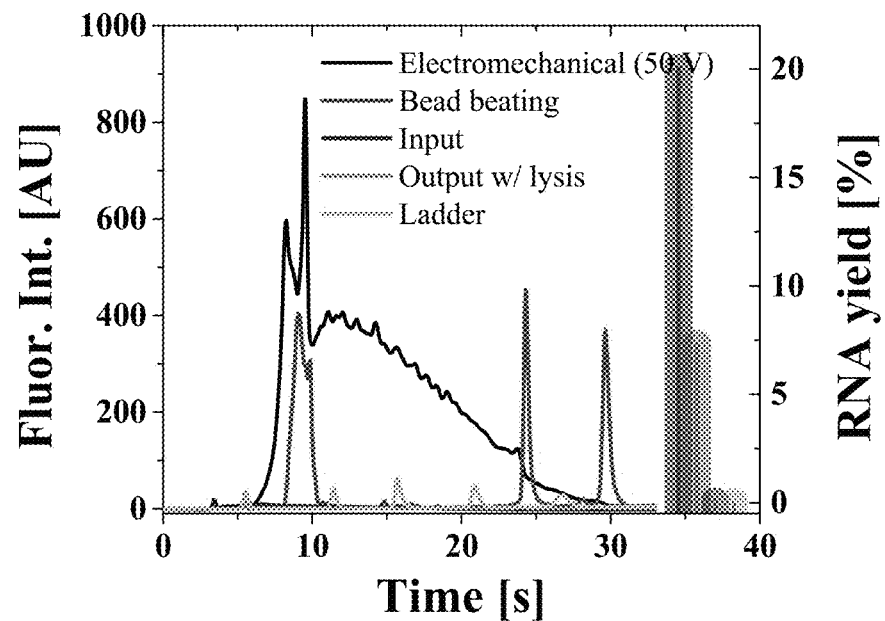
FIG. 6A-6B, collectively referred to herein as FIG. 6, views A and B: A) RNA recovery from easy-to-lyse E. coli bacteria cells; B) RNA recovery from hard-to-lyse M Smeg bacteria cells.
Figure 6B:
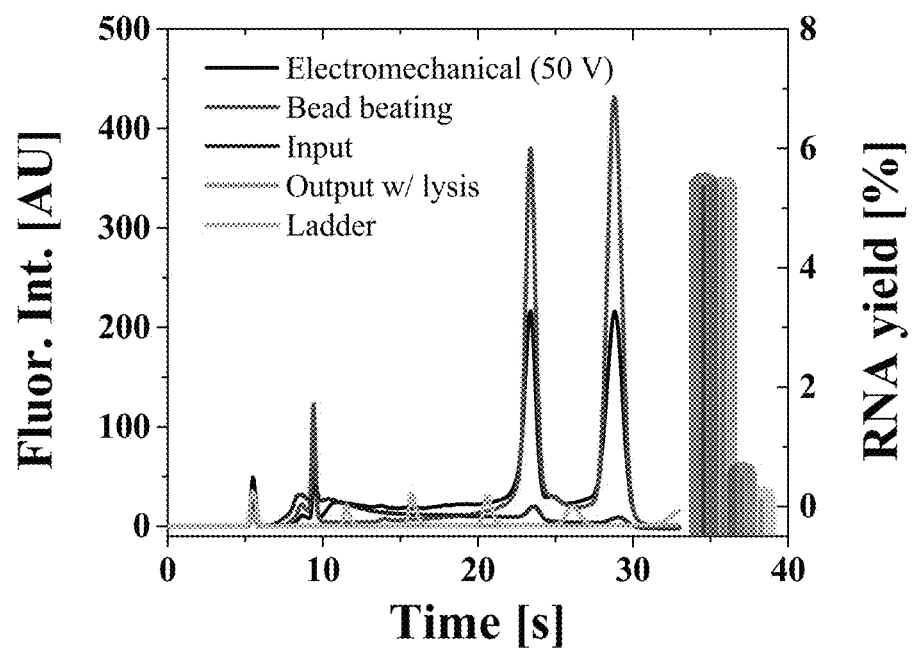

After achieving the recovery of readily detectable lysates such as GFP, we performed bacterial lysis to secure more challenging and invisible lysates such as RNAs that can play an important role in clinical and cellular studies[1]. FIG. 6A shows RNA profile and yield obtained from pathogenic E. coli samples (~4×10[8] cfu/mL) by using on-chip gel electrophoresis and NanoDrop assay, respectively. Electromechanical lysis and a gold-standard lysis protocol (bead beating) were performed separately to generate 100 μL lysis samples in 15 mM PBS, which were then analyzed to compare the RNA profiles and yields. Interestingly, the RNA gel profile obtained by the electromechanical lysis showed the higher first peak than the one recovered by the bead beating although the second and third peaks were unclear. The electromechanical lysis exhibited a higher RNA yield than the bead beating as confirmed by using NanoDrop-based absorbance tests. All RNA samples were appropriately handled and purified before the RNA gel electrophoresis and Nanodrop assays. FIG. 6B shows extraction of RNAs from a mycobacterium strain (M smeg), one of the hard-to-lyse microbes, as they have a heavy and thick outer layer that can be resilient to mechanical, chemical, and enzymatic lysis[30]. The RNA profile clearly showed three peaks comparable to the bead beating results with similar RNA recovery rates of approximately 5% of the theoretical maximum. It is therefore shown that the electromechanical lysis enabled extraction of RNAs as efficiently as the gold standard method, from both easy-to-lyse and hard-to-lyse bacterial species by only using a small electric potential (50 V). Notably, the positive control using the bead beating was also assisted by other lysis mechanism such as freeze-thaw[31] and chemical lysis (RLT buffer)[32], while the novel electromechanical methods performed without any pretreatments.

Parallelization for High-throughput Operation

Figure 7A:
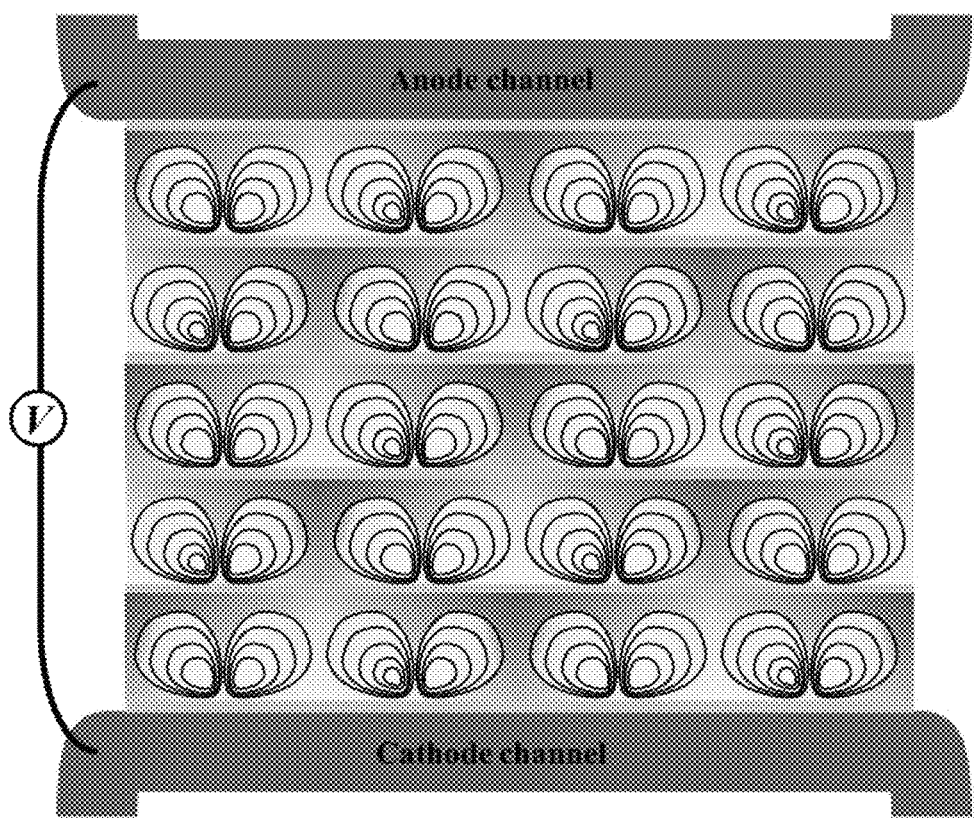
FIG. 7A-7B, collectively referred to herein as FIG. 7, views A and B: A) Depiction of scaling through parallelized architecture; B) Microscopic imaging of parallelized channels showing vortex activity.
Figure 7B:
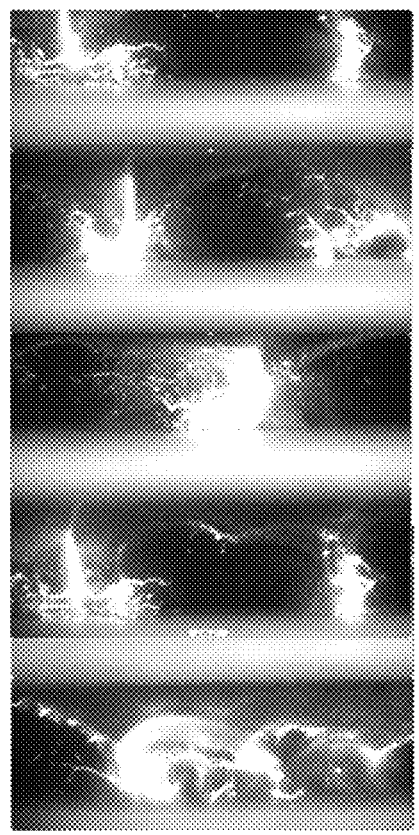

Another unique advantage of the electromechanical lysis is the scalability by laterally parallelizing the single lysis unit, CEM and lysis channel. This is achieved by employing a unipolar ISM (cation exchange) so that the system is symmetrical and has low complexity, thereby enabling simple stacking and/or parallelization. To demonstrate the scalability, a laterally-arrayed electromechanical lysis device was constructed, consisting of six CEMs and five individual lysis channels, all connected by a common inlet and outlet (FIG. 7A). The parallelization architecture directly increased the lysis throughput without the necessity of additional electrode sets, although a higher electric potential was required to maintain the same field strengths in each lysis channel. As shown in FIG. 7B, the parallelized lysis channels showed almost equivalent vorticity and ICP phenomena, indicating similar lysis efficiency and lysate yields in each channel. In addition, the CEMs employed for massive parallelization can minimize non-specific cellular/biomolecular adhesion and clogging due to the same electrical polarity with most biological matters (negative charge)[33], showing efficient lysate isolation and high sustainability for long-term operation[29].

Ultra-high-throughput Device for Water Disinfection

Figures 8A, 8B:
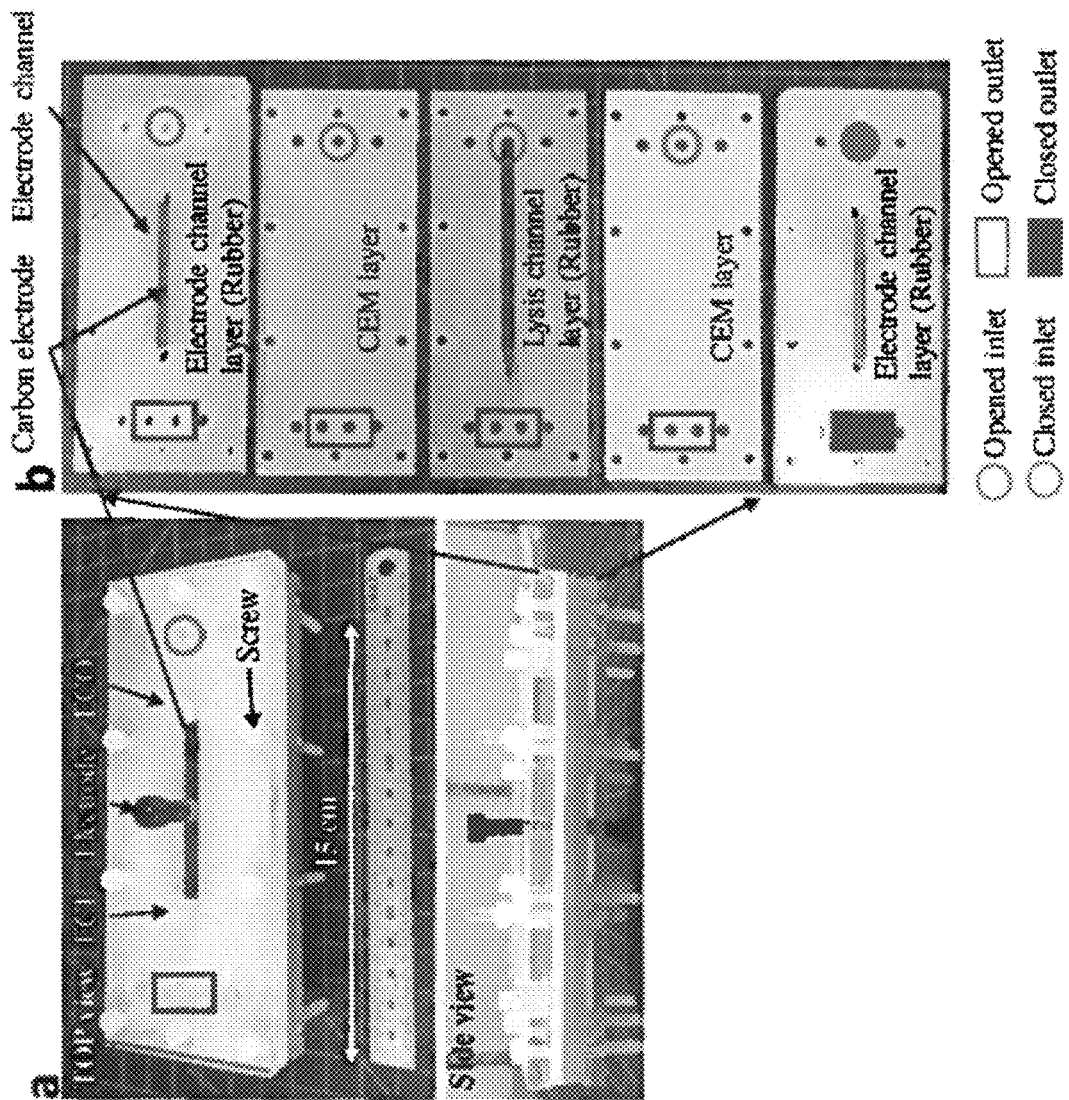
FIG. 8A-8D, collectively referred to herein as FIG. 8, views A, B, C and D: A) Top and side views of high throughput electromechanical lysis configuration; B) Top view of layers comprised in high throughput electromechanical lysis configuration; C) Exploded view of high throughput electromechanical lysis configuration; D) Microscopic imaging of output of high throughput electromechanical lysis configuration.
Figures 8C, 8D:
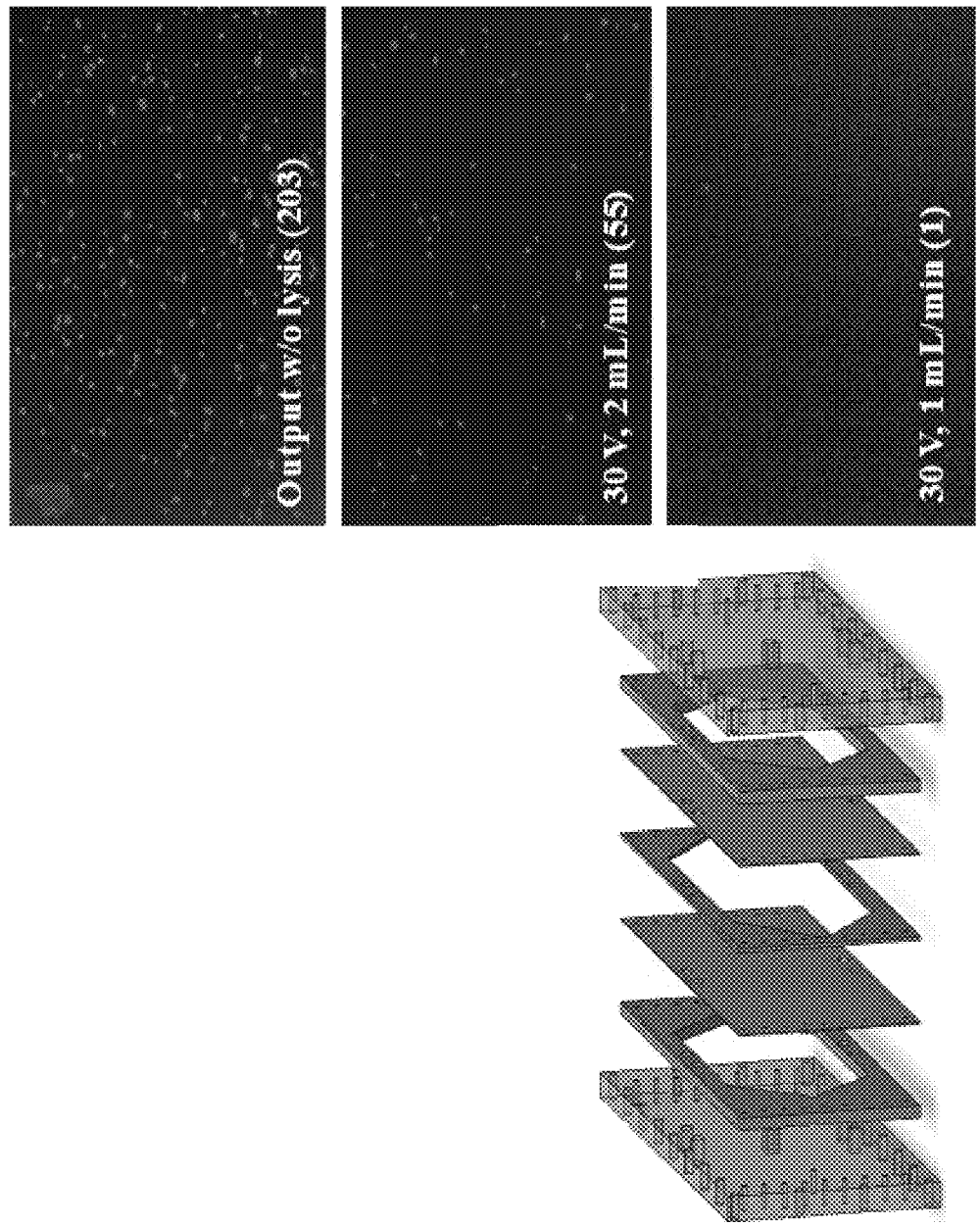

FIG. 8A shows another strategy to enhance the lysis throughput. A large-scale plastic device (15 cm×5 cm) was constructed using a layer-by-layer stacking technique. The large-scale device was far beyond the fabrication limitation of PDMS-based microchips but conserved the same electromechanical lysis mechanism due to the same CEM-CEM distance (~2 mm). Recently, three-dimensional helical vortex formation near ISMs was demonstrated in both theoretical and empirical manners[34], which agrees with the electromechanical lysis in the large-scale device in principle. As shown in FIG. 8B, the lysis channel (12 cm (l)×5 cm (h)) was grooved in a 3-mm-thick conformal rubber sheet and sandwiched by two CEM layers which were then each covered with another rubber and plastic composite layer for the electrolyte channels (8 cm (l)×5 cm (h)) and electrode interfaces. FIG. 8C shows an exploded assembly view of the layers. The layers are mechanically clamped using screws adjusted to both prevent fluid leakages and to compress the compliant lysis layer from 3 mm to 2 mm. During the clamping process, the thickness of the lysis channel layer in the large-scale platform was matched with the lysis channel width in the microfluidic device. That is, the same CEM-CEM distance (~2 mm) was maintained, but the height and length of the lysis channel were substantially scaled up over a few tens of centimeters (used as an example but not a limitation). FIG. 8D shows bacterial lysis results obtained by applying 30 V with extremely high flow rates (few mL/min) compared to the microfluidic electromechanical device (~100 µL/min) and other electrical lysis methods (<1µL/min), resulting in removal of more than 99% of bacterial cells. The bacterial images were obtained by collecting lysis solutions for ~10 min in each condition, and introduced the lysed solution into a straight microchannel having 25 µm height.

This large-scale device may require further engineering for accurate biomolecular applications but would be highly attractive to secure non-sensitive intracellular metabolites and/or to sterilize large-volume solutions in a cost-effective, energy-efficient, portable, and ultra-high-throughput manner. The throughput (over mL/min) and power consumption (~0.5 Wh/L in 1.5 mM PBS) obtained in this work is highly competitive to not only other electrical lysis techniques that required extremely high electric fields (~10-20 kV/cm), but also other sterilization techniques such as ultraviolet light irradiation (~0.2 Wh/L)[35] or heat treatment (e.g., autoclave). Other potential uses include water disinfection, wastewater treatment, aquarium cleaning and food/beverage sterilization.

A novel electromechanical lysis mechanism was presented that can be versatilely available for various bacterial cells, providing highly efficient collection of lysates in a rapid, continuous, and programmed manner by only applying a small electrical field (<100 V/cm). In this work, it was demonstrated for the first time that the ICP phenomena near ISMs facilitated electrical lysis of bacterial cells due to formation of anomalously strong electroconvective vortexes. The vortex can be spontaneously generated without additional treatments by applying an overlimiting potential, and contributed to concentrating and agitating bacterial cells toward the ISM walls where the cell underwent additional mechanical shearing and bombardment by the membrane. Lysis of bacterial cells was achieved by only applying a few tens of volts in a highly salted buffer (e.g., 150 mM) and by maximizing the mechanical and electrical synergic effects. This enabled high recovery rates of valuable intracellular biomaterials such as proteins (>75% yield) and RNAs (>5% yield). The electromechanical lysis operated in a continuous and programmed fashion, which seems to be highly advantageous for integration with other microfluidic modules for on-line downstream assays. It was also demonstrated that the microfluidic lysis device can be highly scaled-up toward multiscale fluidic platforms using layer-by-layer assemble of fluidic channels and ISMs, resulting in ultra-high-throughput electromechanical water disinfection (>99% removal rate) in a power-efficient and portable manner. It is believed that the proposed novel lysis mechanisms will facilitate not only fundamental studies in microbiology due to efficient recovery of intracellular contents (e.g., proteins, nucleic acids, metabolites, drugs, antibodies, bioplastics, and biofuels), but also industrial applications for ultra-high-throughput and portable water disinfection for pathogenic wastewater treatment, aquarium sanitation, and food/water sterilization.

EXPERIMENTAL

Fabrication and preparation of microfluidic devices. The ISM-integrated microfluidic device was fabricated and prepared according to our previous protocols[25, 29]. Briefly, a 3-dimensional (3D) master mold was prepared using a stereolithographic technique (3D Systems Inc., Rock Hill, S.C., USA), followed by a standard soft lithography process using PDMS elastomer kits (Dow Corning, Midland, Mich., USA). The PDMS prepolymer mixed with the curing agent in 10:1 (w/w) ratio, which was poured onto the 3D printed master mold and cured in a 65° C. convection oven over 4 h. After curing, the top PDMS replica was integrated with two CEMs (Fumasep FTCM-E, FuMA-Tech GmbH, Germany) by inserting the membrane into the membrane slots, followed by irreversible bonding with the bottom PDMS block by an oxygen plasma (Harrick Plasma, Ithaca, N.Y., USA). Then, the electrolyte and lysis channels were filled with deionized water over 48 h at room temperature. This allowed volume expansion of the ISMs by swelling, forming a tight seal between ISMs and the membrane slots. All lysis channels were coated with 0.01% Pluronic surfactant (F-127, Sigma-Aldrich, Natick, Mass., USA) to minimize non-specific binding between the cells and PDMS surfaces. Then, the channels were flushed again with 1×PBS to remove the residual chemicals and impurity before loading the cells.

Fabrication of the large-scale device. The large-scale plastic-based device was made of the CEMs, carbon electrodes (Fuel Cell Store, Inc., Boulder, Colo., USA), silicon rubber (3.8 mm thickness) and acrylic sheets (5 mm thickness, McMaster-Carr, Elmhurst, Ill., USA). First, the electrolyte and lysis channels and holes were formed in the plastic and rubber sheets by a laser and manual cutting, respectively. Then each layer including CEMs was assembled by a mechanical clapping. After fabrication, all membranes were filled with demineralized water over 48 h and coated with Pluronic surfactant in the same manner with experiments on the microdevices.

Preparation of bacterial cells. We used constitutively GFP-expressing recombinant E. coli, K12 strain to characterize the lysis performances by fluorescent measurement. The wild-type pathogenic strains, E. coli and M smeg, were used for the RNA recovery experiments. The same culture and preparation protocols were used for all the cells[36]. Shortly, a single colony grown on a lysogeny broth (LB) agar plate was inoculated in a 5 ml LB medium (Sigma-Aldrich, Natick, Mass., USA), and grown to mid-log phase in a rotary-shaking incubator (200 rpm, 36° C.). The culture was centrifuged at 5000×g for 3 min and diluted into 1× or 0.1×PBS solutions at the appropriate concentration based on optical density measurements of the mid-log cultures. We note that all the cells were carefully handled and incubated to protect cellular contamination.

RNA Extraction by Bead Beating and RNA analysis. The cell culture was centrifuged at 13,000×g for 10 min, were then resuspended in 800 µL of Buffer RLT with 1% Beta-mercaptoethanol (Sigma-Aldrich, Natick, Mass., USA). The mixture was then transferred into a lysing matrix in a bead beating tube on ice and shaken vigorously. Bead beating using Mini-beadbeater-16 (BioSpec Products Inc, Bartlesville, Okla., USA) was conducted 10 times (10×60 s), with a 1 min rest time in between on ice. The mixture was centrifuged at 13,000×g for 15 min at 4° C., and the top aqueous layer was collected. 80 µL of aqueous layer was transfer to new tube and mixed with 160 µL of Ampure RNAclean SPRI bead solution (Beckman Coulter Inc, Indianapolis, Ind., USA). Per the manufacture's protocol, the RNA sample was washed with 70% ethanol twice and finally eluded in 40 µL of Nuclease-free water. The eluate of RNA sample from SPRI beads was analyzed using on-chip gel electrophoresis with RNA Pico Chip (2100 Bioanalyzer, Agilent technologies, Santa Clara, Calif., USA) and NanoDrop assay (ND-1000 Spectrophotometer, NanoDrop Technologies Inc, Wilmington, Del., USA). The eluate from the microfluidic lysis channel was purified and analyzed by the same RNA handling protocol without the RLT treatment and bead beating process.

Experimental setup and data analysis. An inverted fluorescence microscope (IX71, Olympus, Tokyo, Japan) equipped with a CCD camera (ORCA-ER, Hamamatsu Photonics, Shizuoka, Japan) was used to obtain the optical microscopic and fluorescent images using an open source software Micromanager (NIH, Bethesda, Md., USA). A pressure-driven flow was generated by a syringe pump (PHD Ultra, Harvard apparatus, Holliston, Mass., USA) and constant current and voltage were applied and measured by current-voltage source measurement unit (Keithley 236, Keithley Instruments, Ohio, USA). Platinum electrodes (Sigma-Aldrich, Natick, Mass., USA) were used to exclude electrode and reaction overpotential occurred in the electrolyte rinsing channels. For data analysis and post processing of microscopic images, Image J (NIH, Bethesda, Md., USA) and OriginPro 8 (OriginLab, Wheeling, Ill., USA) were used.

REFERENCES

The following references are incorporated herein by reference in their entirety.

1. Barczak AK, et al. RNA signatures allow rapid identification of pathogens and antibiotic susceptibilities. *P Natl Acad Sci USA* 109, 6217-6222 (2012).
2. Kotlowski R, Martin A, Ablordey A, Chemlal K, Fonteyne PA, Portaels F. One-tube cell lysis and DNA extraction procedure for PCR-based detection of *Mycobacterium ulcerans* in aquatic insects, molluscs and fish. *J Med Microbiol* 53, 927-933 (2004).
3. Marcus JS, Anderson WF, Quake SR. Microfluidic single-cell mRNA isolation and analysis. *Anal Chem* 78, 3084-3089 (2006).
4. Sarkar A, Kolitz S, Lauffenburger DA, Han J. Microfluidic probe for single-cell analysis in adherent tissue culture. *Nat Commun* 5, (2014).
5. Nan L, Jiang ZD, Wei XY. Emerging microfluidic devices for cell lysis: a review. *Lab Chip* 14, 1060-1073 (2014).
6. Odumeru J, Gao A, Chen S, Raymond M, Mutharia L. Use of the bead beater for preparation of *Mycobacterium paratuberculosis* template DNA in milk. *Can J Vet Res* 65, 201-205 (2001).
7. Berasaluce A, Matthys L, Mujika J, Antonana-Diez M, Valero A, Agirregabiria M. Bead beating-based continuous flow cell lysis in a microfluidic device. *Rsc Adv* 5, 22350-22355 (2015).
8. Zhang H, Jin WR. Determination of different forms of human interferon-gamma in single natural killer cells by capillary electrophoresis with on-capillary immunoreaction and laser-induced fluorescence detection. *Electrophoresis* 25, 1090-1095 (2004).
9. Taylor MT, Belgrader P, Furman BJ, Pourahmadi F, Kovacs GTA, Northrup Mass. Lysing bacterial spores by sonication through a flexible interface in a microfluidic system. *Anal Chem* 73, 492-496 (2001).
10. Di Carlo D, Jeong KH, Lee LP. Reagentless mechanical cell lysis by nanoscale barbs in microchannels for sample preparation. *Lab Chip* 3, 287-291 (2003).
11. Vandeventer PE, et al. Mechanical Disruption of Lysis-Resistant Bacterial Cells by Use of a Miniature, Low-Power, Disposable Device. *J Clin Microbiol* 49, 2533-2539 (2011).
12. Hou HW, Bhattacharyya RP, Hung DT, Han J. Direct detection and drug-resistance profiling of bacteremias using inertial microfluidics. *Lab Chip* 15, 2297-2307 (2015).
13. Brown RB, Audet J. Current techniques for single-cell lysis. *J R Soc Interface* 5, S131-S138 (2008).
14. Cheng J, et al. Preparation and hybridization analysis of DNA/RNA from *E-coli* on microfabricated bioelectronic chips. *Nature Biotechnology* 16, 541-546 (1998).
15. Lee SW, Tai YC. A micro cell lysis device. *Sensor Actuat a-Phys* 73, 74-79 (1999).
16. Gabriel B, Teissie J. Time courses of mammalian cell electropermeabilization observed by millisecond imaging of membrane property changes during the pulse. *Biophys J* 76, 2158-2165 (1999).
17. Ma S, Bryson BD, Sun C, Fortune SM, Lu C. RNA Extraction from a Mycobacterium under Ultrahigh Electric Field Intensity in a Microfluidic Device. *Anal Chem* 88, 5053-5057 (2016).
18. Wang HY, Bhunia AK, Lu C. A microfluidic flow-through device for high throughput electrical lysis of bacterial cells based on continuous dc voltage. *Biosens Bioelectron* 22, 582-588 (2006).
19. Lu KY, Wo AM, Lo YJ, Chen KC, Lin CM, Yang CR. Three dimensional electrode array for cell lysis via electroporation. *Biosens Bioelectron* 22, 568-574 (2006).
20. Lee DW, Cho YH. A continuous electrical cell lysis device using a low dc voltage for a cell transport and rupture. *Sensor Actuat B-Chem* 124, 84-89 (2007).
21. Lu H, Schmidt MA, Jensen KF. A microfluidic electroporation device for cell lysis. *Lab Chip* 5, 23-29 (2005).
22. Mernier G, Piacentini N, Braschler T, Demierre N, Renaud P. Continuous-flow electrical lysis device with integrated control by dielectrophoretic cell sorting. *Lab Chip* 10, 2077-2082 (2010).
23. Vickers DAL, Ouyang MX, Choi CH, Hur SC. Direct Drug Cocktail Analyses Using Microscale Vortex-Assisted Electroporation. *Anal Chem* 86, 10099-10105 (2014).
24. Kim M, Jia M, Kim T. Ion concentration polarization in a single and open microchannel induced by a surface-patterned perm-selective film. *Analyst* 138, 1370-1378 (2013).
25. Kwak R, Pham VS, Lim KM, Han JY. Shear Flow of an Electrically Charged Fluid by Ion Concentration Polarization: Scaling Laws for Electroconvective Vortices. *Phys Rev Lett* 110, (2013).

26. Davidson SM, Wessling M, Mani A. On the Dynamical Regimes of Pattern-Accelerated Electroconvection. *Sci Rep-Uk* 6, (2016).

27. de Valenca JC, Wagterveld RM, Lammertink RGH, Tsai PA. Dynamics of microvortices induced by ion concentration polarization. *Physical Review E* 92, (2015).

28. Khair AS. Concentration polarization and second-kind electrokinetic instability at an ion-selective surface admitting normal flow. *Phys Fluids* 23, (2011).

29. Kim B, et al. Purification of High Salinity Brine by Multi-Stage Ion Concentration Polarization Desalination (vol 6, 31850, 2016). *Sci Rep-Uk* 6, (2016).

30. Hoffmann C, Leis A, Niederweis M, Plitzko JM, Engelhardt H. Disclosure of the mycobacterial outer membrane: Cryo-electron tomography and vitreous sections reveal the lipid bilayer structure. *P Natl Acad Sci USA* 105, 3963-3967 (2008).

31. Johnson BH, Hecht MH. Recombinant Proteins Can Be Isolated from *Escherichia-Coli*-Cells by Repeated Cycles of Freezing and Thawing. *Bio-Technol* 12, 1357-1360 (1994).

32. Chen YT, Sonnaert M, Roberts SJ, Luyten FP, Schrooten J. Validation of a PicoGreen-Based DNA Quantification Integrated in an RNA Extraction Method for Two-Dimensional and Three-Dimensional Cell Cultures. *Tissue Eng Part C-Me* 18, 444-452 (2012).

33. Schott H. Electrokinetic Studies of Bacteria.4. Effect of Acridines on *Streptococcus-Faecalis*. *J Pharm Sci* 63, 48-53 (1974).

34. Pham SV, Kwon H, Kim B, White JK, Lim G, Han J. Helical vortex formation in three-dimensional electrochemical systems with ion-selective membranes. *Physical Review E* 93, (2016).

35. Song K, Mohseni M, Taghipour F. Application of ultraviolet light-emitting diodes (UV-LEDs) for water disinfection: A review. *Water Res* 94, 341-349 (2016).

36. Kim M, Lim JW, Kim HJ, Lee SK, Lee SJ, Kim T. Chemostat-like microfluidic platform for highly sensitive detection of heavy metal ions using microbial biosensors. *Biosens Bioelectron* 65, 257-264 (2015).

While this invention has been particularly shown and described with references to preferred embodiments thereof, it will be understood by those skilled in the art that various changes in form and details may be made therein without departing from the scope of the invention encompassed by the appended claims. Unless otherwise indicated, all numbers, for example, expressing quantities and so forth, as used in this specification and the claims are to be understood as being modified in all instances by the term "about."

What is claimed is:

1. A method of lysing a cell membrane comprising the steps:

a. directing a fluid stream containing cells in a channel comprising an inlet and an outlet and defined, at least in part, by at least a first ion exchange membrane and at least a second ion exchange membrane, wherein the ion exchange membranes are juxtaposed and characterized by the same charge;
   b. applying an electric field across the channel at a voltage and duration sufficient to cause helical electroconvective vortex formation across the channel, thereby lysing the cell membranes of the cells;
   c. collecting an output fluid stream comprising lysate from the outlet; and
   d. isolating the lysate from the output fluid stream.

2. The method of claim 1, wherein at least a first and at least a second juxtaposed ion exchange membrane are cationic exchange membranes.

3. The method of claim 1, wherein at least a first and at least a second juxtaposed ion exchange membrane are anionic exchange membranes.

4. The method of claim 1, wherein the channel is a microchannel.

5. The method of claim 1, further comprising the step of concentrating the lysate.

6. The method of claim 5, wherein at least one nonionic porous membrane is located at the outlet of the channel.

7. The method of claim 1, wherein the electric field is created by an electrode and a ground each located external and parallel to the channel.

8. The method of claim 7, wherein the electrode forms a second channel with at least a first ion exchange membrane and the ground forms a third channel with the at least a second ion exchange membranes.

9. The method of claim 8, wherein the second and third channel are filled with an electrolyte solution.

10. The method of claim 1, comprising a plurality or channels in parallel, each defined by an ion exchange membrane.

11. The method of claim 1, wherein the cell membrane is a bacterial cell membrane.

12. The method of claim 11, wherein isolating the lysate comprises isolating bacterial proteins, bacterial nucleic acids, or a combination thereof.

13. The method of claim 1, wherein isolating the lysate comprises isolating intracellular biomolecules.

14. The method of claim 13, wherein the intracellular biomolecules are selected from the group consisting of DNA, RNA, proteins, and bacterial metabolites, or a combination thereof.

15. The method of claim 14, wherein the bacterial metabolites comprise biodiesels, bioplastics, antibiotics, and antibodies.

* * * * *